United States Patent [19]

Boyle et al.

[11] Patent Number: 5,258,294
[45] Date of Patent: Nov. 2, 1993

[54] BIDIRECTIONAL POX VIRUS PROMOTER ELEMENT

[75] Inventors: Bernard D. Boyle, Leopold; Sharad Kumar, Herne Hill, both of Australia

[73] Assignee: Commonwealth Scientific and Industrial Research Organisation, Campbell, Australia

[21] Appl. No.: 582,881

[22] PCT Filed: Feb. 10, 1989

[86] PCT No.: PCT/AU89/00055
§ 371 Date: Oct. 9, 1990
§ 102(e) Date: Oct. 9, 1990

[87] PCT Pub. No.: WO89/07644
PCT Pub. Date: Aug. 24, 1989

[30] Foreign Application Priority Data

Feb. 12, 1988 [AU] Australia .................. PI6721

[51] Int. Cl.$^5$ .................. C12N 15/10; C12N 15/11; C12N 15/86
[52] U.S. Cl. .................. 435/172.3; 536/24.1; 435/235.; 435/320.1; 935/6; 935/8; 935/36; 424/89
[58] Field of Search .................. 435/172.3, 69.1, 235.1, 435/320.1; 536/27; 424/89; 935/6, 34, 36, 65, 8

[56] References Cited

PUBLICATIONS

Hanggi, M. et al., 1986, *Embo Journal* vol. 5 pp. 1071–1076.
Esposito, J. J. et al., 1989, Advances in Veterinary Science and Comparative Medicine, vol. 33, pp. 195–247.
Onuma et al., *Am. J. Vet. Res.*, 45:112–1218 (1984).
S. Berger et al., *Guide to Molecular Cloning Techniques: Methods in Enzymology*, 152:113–129 (1987).
Boyle, D. B. et al., 1986, *J. Gen. Virol.*, vol. 67, pp. 1591–1600.
Boyle, D. B. et al., 1988, *Virus Research*, vol. 10, pp. 343–356.
Tsao, H. et al., 1988, *J. Virol.*, vol. 62, pp. 4832–4834.
Tomley, F. et al., 1988, *J. Gen. Virol.*, vol. 69, pp. 1025–1040.

*Primary Examiner*—Richard A. Schwartz
*Assistant Examiner*—Mary E. Mosher
*Attorney, Agent, or Firm*—Merchant & Gould

[57] ABSTRACT

A gene sequence including a first promoter for the expression of a major early fowlpox virus (FPV) protein. In a preferred aspect, the gene sequence further includes a second promoter for the expression of a late fowlpox virus protein in opposite orientation to said first promoter. The promoter is useful in developing FPV based vectors for the delivery of vaccine antigens preferably to poultry, and as a tool to study the temporal regulation of poxvirus genes. The invention also offers methods useful in the construction of recombinant fowlpox viruses or related avian poxviruses, which methods are characterized by the introduction of foreign DNA into the fowlpox virus or into virus DNA sequences, which sequences are able to use native FPV promoter regions.

9 Claims, 13 Drawing Sheets

```
         10         20         30         40         50         60
GGTCCTAAAT TTTGGTGGAT AAGGCAAATT ACTGCTTTGT TGATTGTTAA ATCTATTAAG 70         80         90        100        110        120
AAAACTGGTA AAAATACCAG CAGTATCGTT ACTACGTAAT ATAGATATCA TTCTATCCTG 130        140        150        160        170        180
AATAGACCTA CTATCGTCTG TATTGTATTC GTCTACTATA GATTCCTTCT CATTTCTACT
                                    AccI                PRIMER 4

190        200        210        220        230        240
ATCATCTTCA TCTAGCTTTT CTGAAAATAT CTCTGGATTA TTACTAACAT TACGTTTGAT 250        260        270        280        290        300
TCTAGAAATA AAATCTTTGT GGAAGTTCTC AGCCATTTAG TATCCTAAAA TTGAATTGTA
                                       ORF 3

310        320        330        340        350        360
ATTATCGATA ATAAAATGGAC AATTCTATGG ATATTAACGA TATACTACTG TCAGATGATA
  ClaI       ORF 2

370        380        390        400        410        420
ACGATTATAA GAGTTACGAT GAAGATGATG ACTCTATATC CGATATAGGA GAAACAAGTG
                                                PRIMER3

430        440        450        460        470        480
ATGATTGTTG TACGACTAAA CAATCGGATT CCAGGATAGA ATCTTTCAAG TTCGATGAAA 490        500        510        520        530        540
CTACTCAATC ACCTCATCCA AAACAATTGA GCGAAAGGAT AAAGGCTATA AAACAACGAT 550        560        570        580        590        600
ACACTAGACG TATAAGCCTA TTTGAAATAA CTGGAATTTT ATCCGAAAGT TATAATTTAT
```

FIG. 3A

```
       610        620        630        640        650        660
TACAACGTGG AAGAATTCCA TTACTTAATG ACCTGACAGA AGAAACGTTT AAAGATTCAA
                EcoRI
       670        680        690        700        710        720
TTATTAATAT TATGTTTAAA GAAATAGAAC AAGGAAATTG TCCTATAGTT ATACAAAAGA
       730        740        750        760        770        780
ATGGAGAACT TTTATCCTTA ACCGACTTTG ATAAAAAAGG AGTACAGTAT CATCTGGACT
       790        800        810        820        830        840
ACATTAAAAC TATATGGCGT AACCAACGTA AATTATAATT TAGATATATA ATGTTCTTGA
                                       ORF1 ORF2
       850        860        870        880        890        900
ATAAAATCGA ATATGAATTC TATATCTACA GCATTTCTT  TATAGTTAAT GTTGTAATTA
                EcoRI
       910        920        930        940        950        960
TCGGTTATAC ATTGAACAAT TGATATAAGT GTTGTTTTGT GCTTTTCATA TTCTTCCACA
       970        980        990       1000       1010       1020
AATATGTTTT TATACATTTC ACGGTTATTT GATATCTCAC TTATCAATCC CTGAATGTTA
      1030       1040       1050       1060       1070       1080
TTAACCTTTC TTTTCTTTAA ATCTTCTACG GAAACTTTAG TCTTAAATGA TGCCATTATT
      1090       1100       1110       1120       1130       1140
TCACTAAAAA GAACGTGTAA GCGTTCGTTA GTAAGTATTT CAGAATACAC TATACTAGAG
```

FIG. 3B

```
      1150       1160       1170       1180       1190       1200
AGTTTAGAAA ATATGTTAAC AAATTGTGTT GTTTTGACAC AGCTAGTTTG AAATAAAATA 1210       1220       1230       1240       1250       1260
ATATTAGGTA ATACCTTTTT AAAGAAGCTT ACGTATTTAT TATTTATCTG GTCTATACCG 1270       1280       1290       1300       1310       1320
TCTATCGTTA TATCGCAGAA ACACTTAATA CCAAATATTA CGTTTTCTTT AGAGAAAGAA 1330       1340       1350       1360       1370       1380
AATACATCTT TATATCTTC AGTTTTATC TTATCAGATA CTACATCTGT ATTAAAAAGT 1390       1400       1410       1420       1430       1440
GCAATTATCT TTATGATATA ATTGCTATCC GCTAGGACTT TATTTATTGT TCTGATAATG 1450       1460       1470       1480       1490       1500
AAACTATTGT TTTCCATTAA TATTTTGTAA GCTTGATGTT CGTTATTAGC ACTTTTAATT 1510       1520       1530       1540       1550       1560
AACGACACAA TTCCTAGTAT CTTTTTAAA TCCTGCACTA TTTCATTTGT ATCTTTTTTC 1570       1580       1590       1600       1610       1620
ATATTAGAGT ACATATTGTT TATAGATGTA ATAACTTTTG CATATACTAA CATATCTTTA 1630       1640       1650       1660       1670       1680
AATATTCTGA TAAACTGTTC TTTTGTTTCT TTATCTGTTA TTTTGTTGAG CATAGATTTT
```

FIG. 3C

```
      1690       1700       1710       1720       1730       1740
ACGTTGCCG CTGATCGCAT ATACCAAAAT GTAAACATCT TGAATTCTAC TTGCTGCATG
          ─────────PRIMER 2─────────▶
      1750       1760       1770       1780       1790       1800
GCTAGAATAA CAGTCTCGTC AGACATTGCG CAGTTAATAT CACCGCCTAT CTTACTTTCT
          ─────────PRIMER 1─────────▶
      1810       1820       1830       1840       1850       1860
AGAATAGGAA AAACCGTTAA AAATGAATCG ATATCATTAT CATAATTTAC TTCATACACT
                      ORF1       ClaI
                      ▼
      1870       1880       1890       1900       1910       1920
TTTTGACCTG TACTATTCTC TAAATACTTC TTACTTAATT CATAAAATTC AATAAATGCA 1930       1940       1950       1960       1970       1980
TTCCTGAACT TTCCATGAT TTATAGCTTG TAGTATTTTT CTAATATTGA TTTGATTTGT

1990       2000       2010       2020       2030       2040
ATATGTGTAT AATCTTTACC GATACCTAAT TTAAGCATAG TATTAATAAC CCAAGTTTTT 2050       2060       2070       2080       2090       2100
ATAAATATTT CTTTGTTATC GGTTACCACA TATTTAAATA CTGAATTAAA GTATTTAACT 2110       2120       2130       2140       2150       2160
ATAGGATTAT TCTGAGTAGA TATATTATCC ATAAATACAG ACCGTTTTGT AGATAGAGGT 2170       2180
TCTGTAAATA ATTCACCGTC GAC
                       SalI
```

5'-ATTTAGTATCCTAAAATTGAATTGTAATTATCGATAATAAAT → EARLY
3'-ATTTATTATCGATAATTACAATTTTAGGATACTAAAT → LATE

FIG. 9

BIDIRECTIONAL POX VIRUS PROMOTER ELEMENT

This invention relates to recombinant vectors and their construction, and in one aspect this invention relates to recombinant fowlpox virus vectors and use thereof.

Poxviruses are large DNA viruses which replicate within the cytoplasm of infected cells. The vaccinia virus is the most widely studied member of the poxvirus family and has been widely used to express a number of foreign genes inserted into the vaccinia virus genome. In recent years, recognition of non-essential regions of the vaccinia virus genome, followed by mapping and nucleotide sequence determination, has made it possible to insert and express a wide variety of foreign genes through the medium of recombinant vaccinia viruses. Such recombinant vaccinia viruses have the potential to deliver vaccine antigens to a variety of animal species. However, for faithful expression of an inserted gene, it is important to position the gene near unique viral promoter regions.

A recognised problem resides in a risk of cross species infection and therefore the spread of disease from one animal species to another through the widespread use of vaccinia virus in animals. Thus, the construction of recombinants based on host specific poxviruses is desirable, e.g. fowlpox virus for poultry or ORF for sheep vaccines. Although promoter sequences have been described for a number of early and late genes of vaccinia viruses, little is known about promoter regions in other pox viruses. In order to construct host specific live viral vaccines, it is of fundamental importance that the molecular biology of those viruses, and in particular the biology of transcriptional control elements or promoter region(s) in the pox virus be understood. Therefore, it is necessary to characterise and isolate these regions before utilising them in suitable recombinant vectors. Such vectors show great potential for the manufacture of viral vaccines and the like.

Accordingly, it is an object of the present invention to overcome, or at least alleviate, one or more of the deficiencies and/or difficulties related to the prior art.

Accordingly, in a first aspect of the present invention there is provided a gene sequence including a first promoter for the expression of a major early fowlpox virus protein.

In a preferred aspect of the present invention, the gene sequence further includes a second promoter for the expression of a late fowlpox virus protein in opposite orientation to said first promoter.

The gene sequence may be approximately 40 base pairs in length, consisting of two promoter elements in opposite orientation to each other.

As stated above, this promoter sequence, in its preferred form, is characterised in that it has a major early function and a late function in opposite orientation to the early function. The early function of the promoter compares well with the strongest known promoter of vaccinia virus (PL11). Because of the strength of this promoter and its unique bidirectional nature, it has important applications in the construction of both vaccinia (VV) and FPV vectors and other recombinant poxviruses for the delivery of foreign antigens. Its small and defined size makes it a versatile DNA element which may express two foreign genes of interest simultaneously in a pox virus expression system as described below. Since its early function compares well in strength with PL11, a VV promoter widely used for expression of foreign genes during late stages of virus growth cycle, it may be a promoter of choice when high levels of expression is required during early stages of virus growth. Its promoter strength is 3-4 times greater than the VV P7.5 promoter which has been widely used, to date, to express genes in recombinant VV, FPV and other poxviruses (for a review see Moss and Flexner, 1987). The gene sequence may be particularly useful to induce cytotoxic T-lymphocyte (CTL) response to an expressed antigen since late promoter expressed gene products appear not be recognised by CTL (Coupar et al, 1986). Being a FPV native promoter, it may be a promoter of choice in developing FPV based vectors for the delivery of vaccine antigens preferably to poultry.

Finally, because of its small and defined size and its unique structure, it may provide an important tool to study the temporal regulation of poxvirus genes.

In a further preferred aspect of the present invention there is provided a gene sequence including a first promoter for the expression of a major early fowlpox virus protein.

Accordingly, in a preferred aspect there is provided a plasmid selected from plasmids pSK06 and pSK07 as hereinbefore described.

Samples of purified DNA containing the plasmid pSK06 were deposited with the Australian Government Analytical Laboratories of 1 Suakin Street, Pymble, New South Wales, 2073, Australia, on Feb. 9, 1989 and have received the deposition number N89/004621.

The viral vector or derivative thereof may be constructed using a suitable plasmid cloning vector. Suitable plasmid cloning vectors include pUC8, pUC12, M13-mp8 and -mp9.

The native promoter region and fragment of foreign DNA may be flanked by DNA of non-essential regions of the FPV genome. It will be understood that the use of DNA constructs employing native promoter regions of the fowlpox virus not only makes possible the provision of highly host specific viruses, but also provides for a far more efficient virus in terms of its translational efficiency relative to other recombinant pox viruses, all of which to date have employed foreign promoter regions from other sources to initiate expression of selected genes, e.g. promoter regions from a vaccinia virus source.

Accordingly in a preferred aspect, there is provided a viral vector including a
- portion of the genome of a vector virus;
- a gene sequence including
  - a first promoter for the expression of an early fowlpox virus protein; and
  - a second promoter for the expression of a late fowlpox virus protein in opposite orientation to said first promoter; and
- a first DNA sequence coding for a first foreign gene of interest and under the control of the first promoter.

Preferably the first foreign DNA sequence codes for a first antigen characteristic of an avian disease.

In a preferred embodiment of this aspect of the present invention the viral vector includes alternatively or in addition to said first DNA sequence a second DNA sequence coding for a second foreign gene of interest and under the control of the second promoter.

Preferably the second foreign DNA sequence codes for a second antigen characteristic of an avian disease.

In a particularly preferred form, the portion of the genome of a virus is a portion of the fowlpox virus geneome or vaccinia virus genome.

In a preferred form the plasmid cloning vector may include a DNA sequence of a non-essential region of the FPV genome into which region the suitable native promoter region and fragments of foreign DNA may be inserted.

In this form the native promoter region and promoter of foreign DNA may be flanked by DNA of a non-essential region of the FPV genome.

Accordingly, the viral vector according to this aspect of the present invention may be utilised in the preparation of vaccines, preferably vaccines against avian disease.

In a further aspect of the present invention there is provided a process for the preparation of a viral vector which process includes
  providing
    a viral DNA from a fowlpox virus; and
    a plasmid cloning vector;
  constructing a genomic library from the viral DNA;
  identifying a gene sequence from the genomic DNA library, said gene sequence including
    a first promoter for the expression of a major early fowlpox virus protein; and
    a second promoter for the expression of a late fowpox virus protein in opposite orientation to said first promoter; and
  inserting the gene sequence into a suitable site in the plasmid cloning vector.

In a preferred aspect of the process of the present invention the process may include the step of mapping and sequencing a suitable native promoter region.

In a further preferred aspect of the process of the present invention may further include providing a second suitable plasmid cloning vector
  and subcloning a segment of the first plasmid cloning vector including the native promoter region into the second suitable plasmid cloning vector.

The preferred process may further include further sequencing of the native promoter region.

In a preferred form of the process of the present invention the process may include
  providing
    a first suitable plasmid cloning vector,
    a suitable native promoter region,
    a first segment of DNA encoding a non-essential region of FPV genome,
    a second segment of foreign DNA;
  cloning the first segment into the suitable plasmid cloning vector,
  cloning the native promoter region into the suitable plasmid cloning vector within the first segment of DNA,
  cloning the second segment of foreign DNA into the suitable plasmid cloning vector within the first segment of DNA.

It will be understood in this preferred manner the native promoter region and second segment of foreign DNA may be inserted into viable FPV at a previously established region by virtue of the flanking non-essential region of the FPV genome created as described above.

The thus formed sequence may be inserted into FPV virus infected cells utilising any suitable technique for example homologous recombination.

It is to be understood that while the invention hereinbelow describes the isolation and characterisation of early gene of fowlpox virus and the insertion of fowlpox promoter sequences into a plasmid vector, the technology described is equally applicable to the isolation and characterisation and insertion of other native animal pox virus promoter regions into suitable recombinant plasmids. These plasmids may then be utilised to produce animal pox virus vaccines.

In the first stage of mapping and sequence of the promoter sequence, in a preferred identification early mRNA's coded by the FPV genome was undertaken. Such identification lead to a major approximately 1.0 kb transcript which was mapped to an approximate 1.5 kb ClaI fragment.

The 1.5 kb fragment was cloned into PUC8 and M13 vectors and sequenced.

Accordingly in a preferred embodiment of the present invention there is provided a fowlpox virus vector including an approximate 1.5 kb ClaI fragment cloned into a suitable plasmid or bacteriophage cloning vector. Such cloning vector may include pUC8, pUC12, M13-mp8 and mp9.

Further identification may be undertaken utilising fragments of the clone which may be sub-cloned into other plasmids and sequenced. The dideoxy chain termination method may be used.

Accordingly, in a still further embodiment of the present invention comprises a gene sequence including a late RNA start site and an early RNA start site separated by a short sequence of DNA. The gene sequence may constitute a bidirectional promoter cassette.

In a further aspect, the invention may be utilised to provide an avian disease vaccine comprising recombinant fowlpox virus wherein at least a first foreign DNA sequence encoding an antigen characteristic of the said avian disease has been inserted into a suitable gene of the fowlpox virus or in virus DNA sequences controlling expression of said gene, and under the control of at least a first native fowlpox virus promoter region or regions. Referably two foreign DNA sequences may be included under the control of a bidirectional promoter element on either side in opposite orientation.

It is envisaged that in accordance with the present invention vaccines may become available for protection against a wide variety of avian diseases such as those caused by viruses, bacteria, protozoa, metazoa, fungi and other pathogenic organisms, by insertion of DNA sequences encoding appropriate antigens characteristic of these diseases into the FPV genome as broadly outlined above.

In one aspect, the present invention now makes possible the construction of a biologically safer range of host specific recombinant avian vaccines than hitherto obtainable, which vaccines include native promoter regions of the fowlpox virus.

This invention therefore also offers methods useful in the construction of recombinant fowlpox viruses or related avian poxviruses, which methods are characterized by the introduction of foreign DNA into the fowlpox virus or into virus DNA sequences, which sequences are able to use native FPV promoter regions.

The present invention will now be more fully described with reference to the accompanying examples. It should be understood, however, that the following description is illustrative only and should not be taken in any way as a restriction on the generality of the invention described above.

In the figures

FIG. 2 is a mapping of FPV-PstI fragment F coded early transcripts by northern blot analysis. Total cellular RNA isolated from virus infected cells incubated in presence of AraC was hybridised to gel purified nick translated ClaI fragments of PstI fragment F. A, 1.5 kb; B, 2.0 kb; C, 3.0 kb; D, 4.0 kb and E, 4.8 kb. RNA was electrophoresed on 1.2% agarose, 5.4% formaldehyde denaturing gels and blotted onto Hybond-N nylon membranes prior to hybridization to $^{32}$P-labelled nick translated probes.

FIGS. 3, 3A, 3B and 3C collectively is a sequence of 1.5 kb ClaI fragment and the region around it. Sequence was obtained from both strands by dideoxy method using EcoRI and HindIII subclones of 1.5 kb ClaI fragment in M13. The region upstream and downstream of ClaI sites was sequenced using synthetic primers on ss DNA templates from M13 clones containing the 3.7 kb SalI fragment (see FIG. 1). The translation start and termination sites for the two ORF's, and location of primers used for S1 nuclease analyses are indicated. The RNA start sites for all three genes are indicated by dotted lines. The two promoter element (E and L) described in the text is boxed in this figure.

FIG. 4 is a S1 nuclease analysis of 1.5 kb ClaI fragment. Two ss-M13 DNA clones containing the complementary strands of the ClaI fragments (in mp8 and mp9 respectively) were hybridised to total cellular RNA from uninfected host cells (lanes 1 and 4) or FPV infected cells incubated in the presence (lanes 2 and 5) or absence (lanes 3 and 6) of AraC, followed by treatment with S1 nuclease. Protected fragments were fractionated on 1% alkaline agarose gels, transfered to nylon membranes and hybridised to nick translated $^{32}$P-labelled ClaI fragment. M13 mp8 clone (lanes 1-3) is early RNA like strand, while M13 mp9 clone (lanes 4-6) contains sequence complementary to early gene RNA.

FIG. 5A-B is a mapping of the 5'-end of the ORF1 coded RNA. Total cellular RNA from uninfected CES cells (Lane 2) or FPV infected cells in the presence (lane 3) or absence (lane 4) of AraC was hybridized to $^{32}$P-labelled ss probe (lane 1). For preparation of probes, 2 synthetic primers complementary to ORF1, 424 (Primer 1) and 482 bp (Primer 2) upstream of the ClaI site were extended in the presence of $^{32}$P-dCTP on ss-M13 DNA clone (M13-Sal 3.7), cut with SalI and relevant DNA fragments isolated from sequencing gels. DNA-RNA hybrids were treated with S1 nuclease and protected fragments ran on 6% sequencing gels alongside a sequencing ladder obtained by same M13 DNA template and primers. Panels A and B represent experiments with primers 1 and 2 respectively. The sequence around the 5'-end of the major protected fragments is shown for the RNA like strand. Technical details of S1 nuclease analysis were according to Davis et al, (1986).

FIG. 6 is a mapping of the 5'-end of ORF2 coded RNA. $^{32}$P-labelled ssDNA probe complementary to RNA like strand was prepared by extending a synthetic primer 124 bp upstream of ClaI site on a M13-Sal 3.7 ssDNA clone followed by digestion with EcoRI and isolation of 453 base probe from sequencing gels. Probe (lane 1) was hybridised to RNA isolated from uninfected cells (lane 2), FPV infected cells incubated in presence of 100 ug/ml cycloheximide (lane 3) or 50 ug/ml AraC (lane 4) or without either (lane 5). Following S1 treatment of DNA-RNA hybrids, the protected fragments were analysed on 6% sequencing gel. DNA markers (M) were prepared by $^{32}$P-labelling of HpaII cut pBR322 fragments. Sequencing ladder on the left hand side was obtained by using the same primer and template as used for preparation of hybridization probe. Sequence around the 5'-end of protected fragments is shown for the RNA like strand.

FIG. 7 is a mapping of the 5'-end of ORF3 coded RNA. $^{32}$P-labelled ssDNA probe complementary to the RNA was prepared by extending a synthetic primer 91 bp downstream of ClaI site on a M13-Sal 3.7 ssDNA clone containing the RNA like strand followed by digestion with AccI and isolation of 260 base probe from sequencing gels. Rest of the experimental details were as in FIG. 5. Lane 1, probe alone; lane 2, uninfected cell RNA; lane 3, early RNA (cycloheximide); lane 4, early RNA (AraC); lane 5, late RNA. Markers (M) are same as in FIG. 5. Sequence around two late RNA protected fragments is shown for RNA like strand.

FIG. 8A-C is a construction of the plasmids used in transient expression experiments. Polylinker region of pSK06 containing the promoter element (P) in SalI site is shown in panel A. The direction of early and late transcription are indicated and early and late RNA start sites are underlined. In pSK07, from which pSK09 and pSK22 were delived, the orientation of SalI fragment in relation to polylinker, was opposite to that in pSK06; pSK08 and pSK09 were constructed by cloning E. coli Lac2 gene into the Bam HI site of pSK06 and pSK07 respectively (B). The sequence around promoter-LacZ junction for pSK08 and pSK09 deletion mutants used in transient expression system is also shown. The basic structure of other plasmids used in experiments detailed in Tablet 3 is shown in panel C. In the figures in panel C, promoter and gene fragments are not proportionate to their actual sizes.

EXAMPLE 1

Identification and mapping of the major early gene

Figure 1:
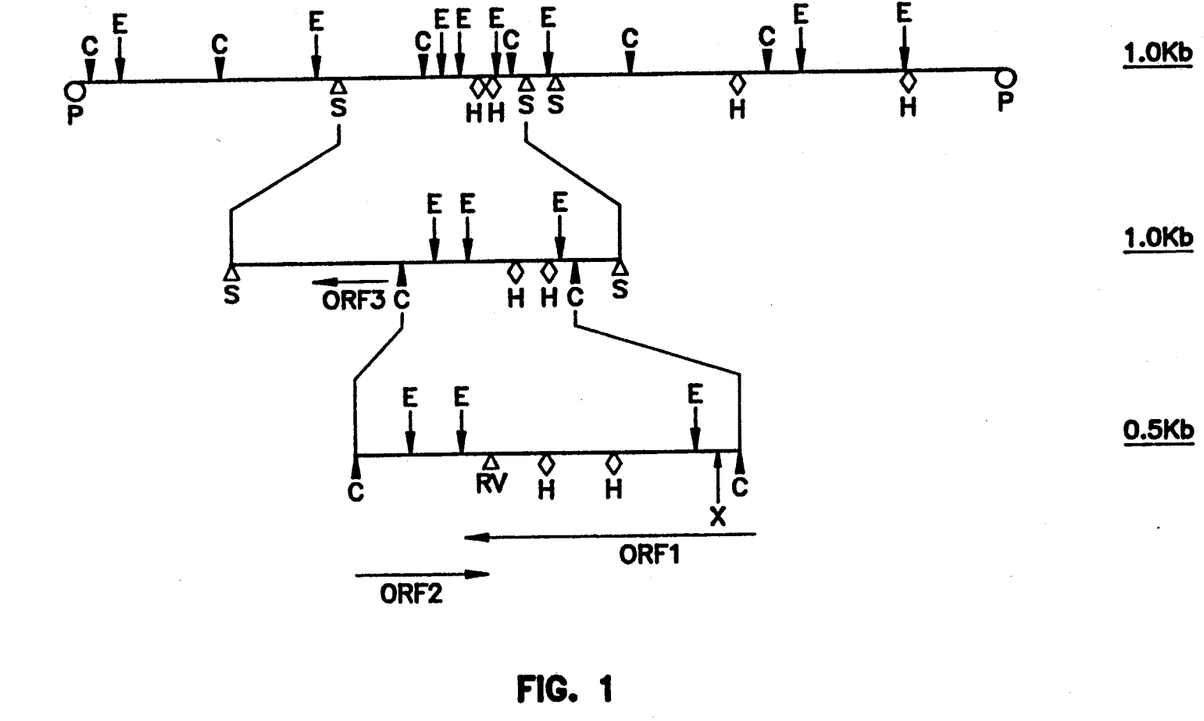
FIG. 1 is a restriction map of PstI fragment F of fowlpox virus genome and mapping of major E-gene within it. The directions of two ORF's within the 1.5 kb ClaI fragment and one upstream of it are indicated by arrows. ORF1 and 3 represent two late genes while ORF2, the major early gene.
Figure 2:
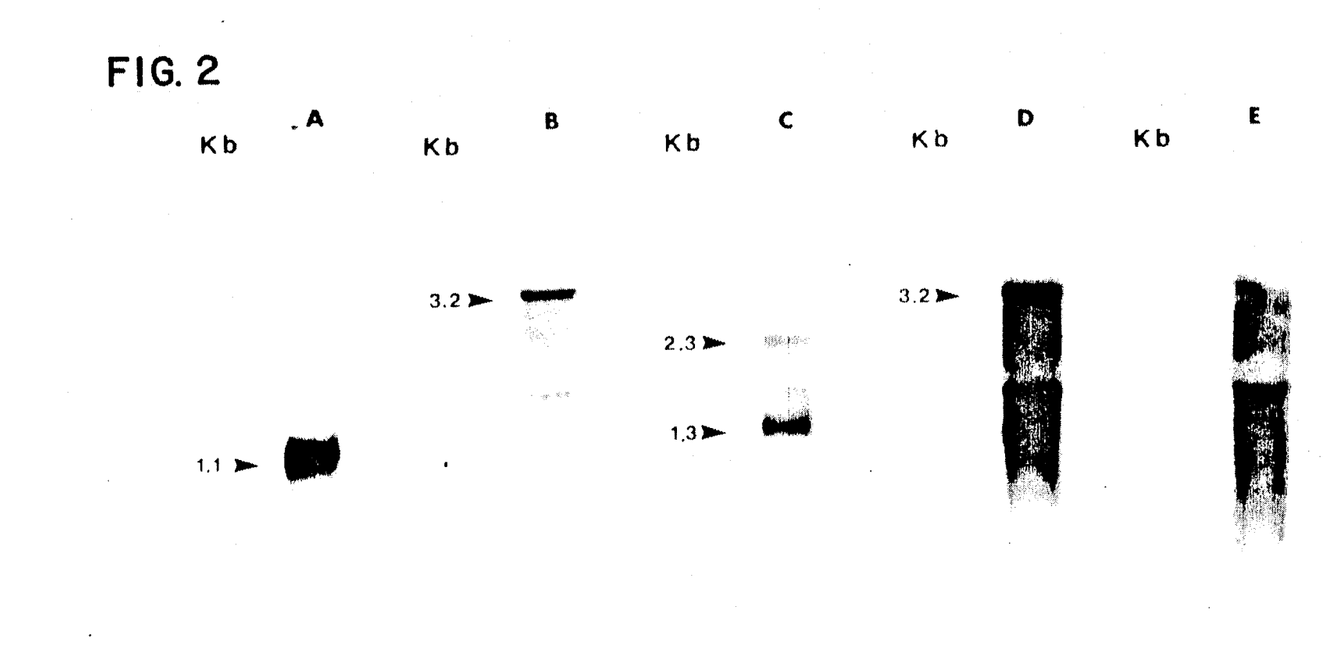

FPV encoded early mRNA's were detected by hybridizing total cellular RNA prepared from FPV infected CES cells grown in the presence of AraC to four cloned PstI fragments of the FPV genome. Four fragments E, F, J and M (20.5, 17.3, 12.5 and 5.7 kb respectively) representing approximately 1/6th of the total genome of FPV (Coupar et al, unpublished) were analysed and eleven early transcripts were identified by norther blot analysis of RNA (Table 1), of which four hybridised to fragment F. The restriction enzyme map of fragment F is shown in FIG. 1. To map the early transcripts within the 17.3 kb fragment F, 5 size fractionated ClaI fragments of 4.8, 4.0, 3.0, 2×2.0 and 1.5 kb respectively were hybridized to early RNA (FIG. 2). The major RNA transcript (approximately 1.0 kb) was mapped to the 1.5 kb fragment. Three other early transcripts of 3.2, 2.3 and 1.2 kb respectively were also detected. The quantity of this transcript is approximately 10 fold higher than any of the other transcripts hybridizing to the four PstI fragments of the FPV genome used in the study.

Sequencing of ClaI Fragment

Figure 3:
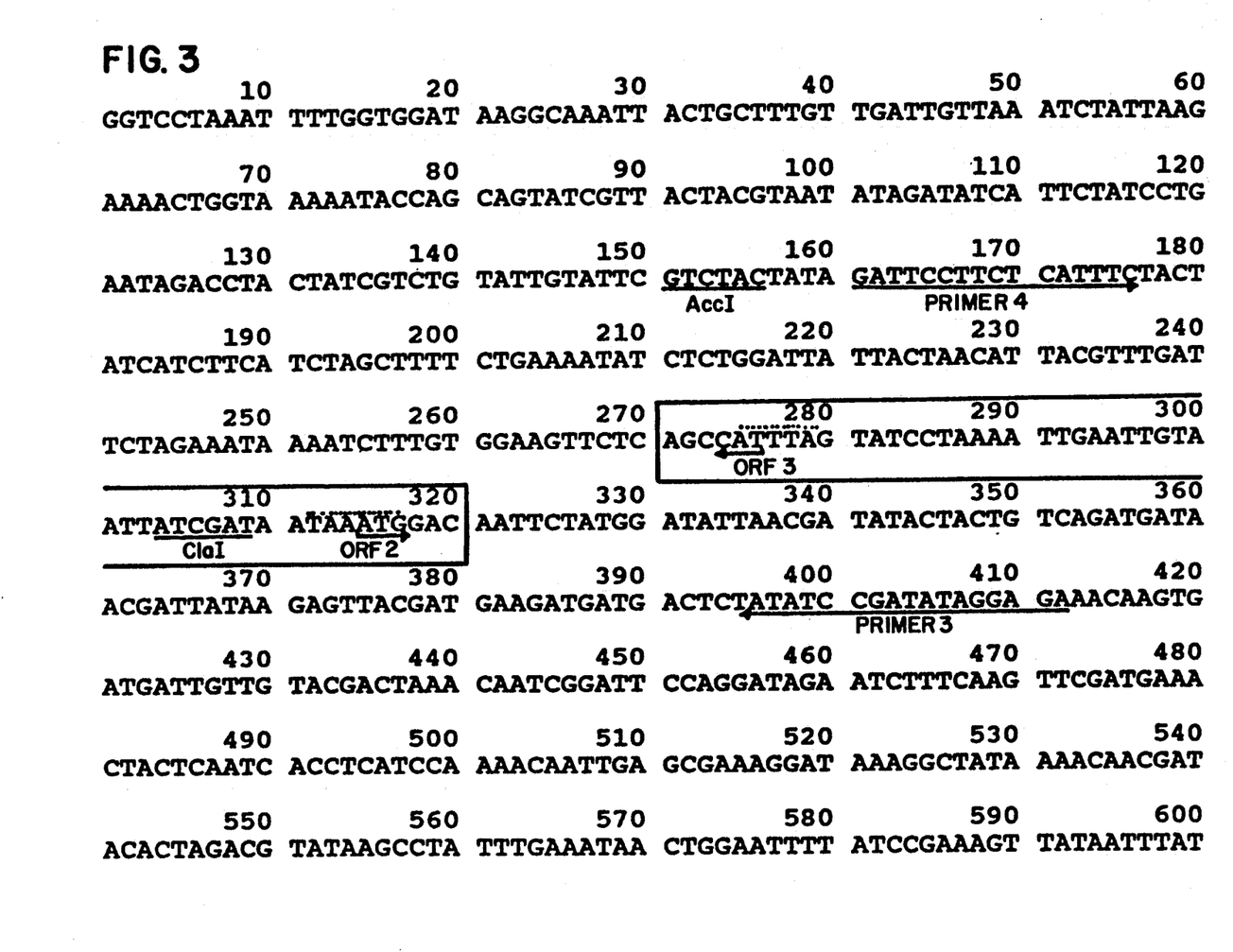
Figure 3A:
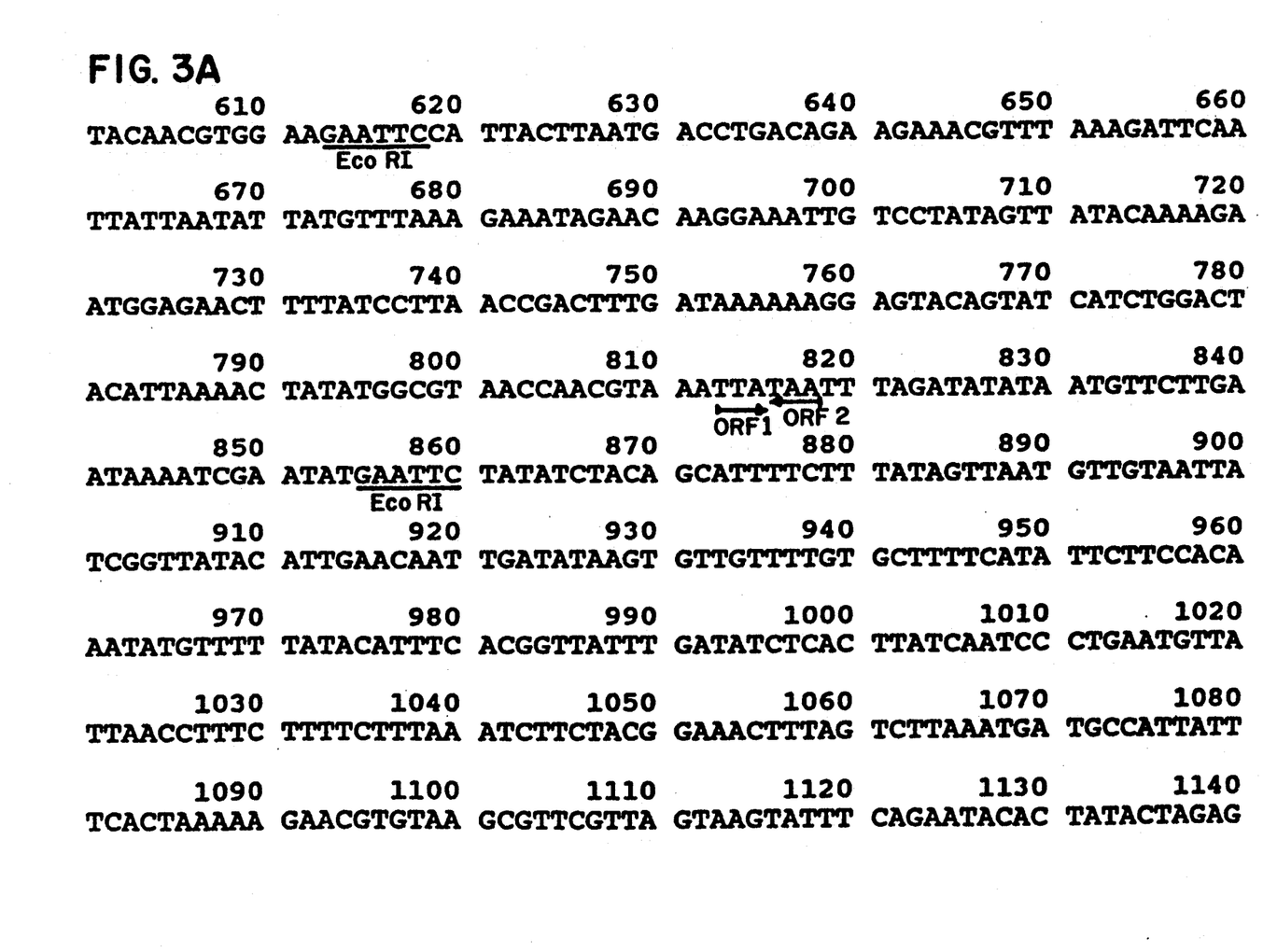
Figure 3B:
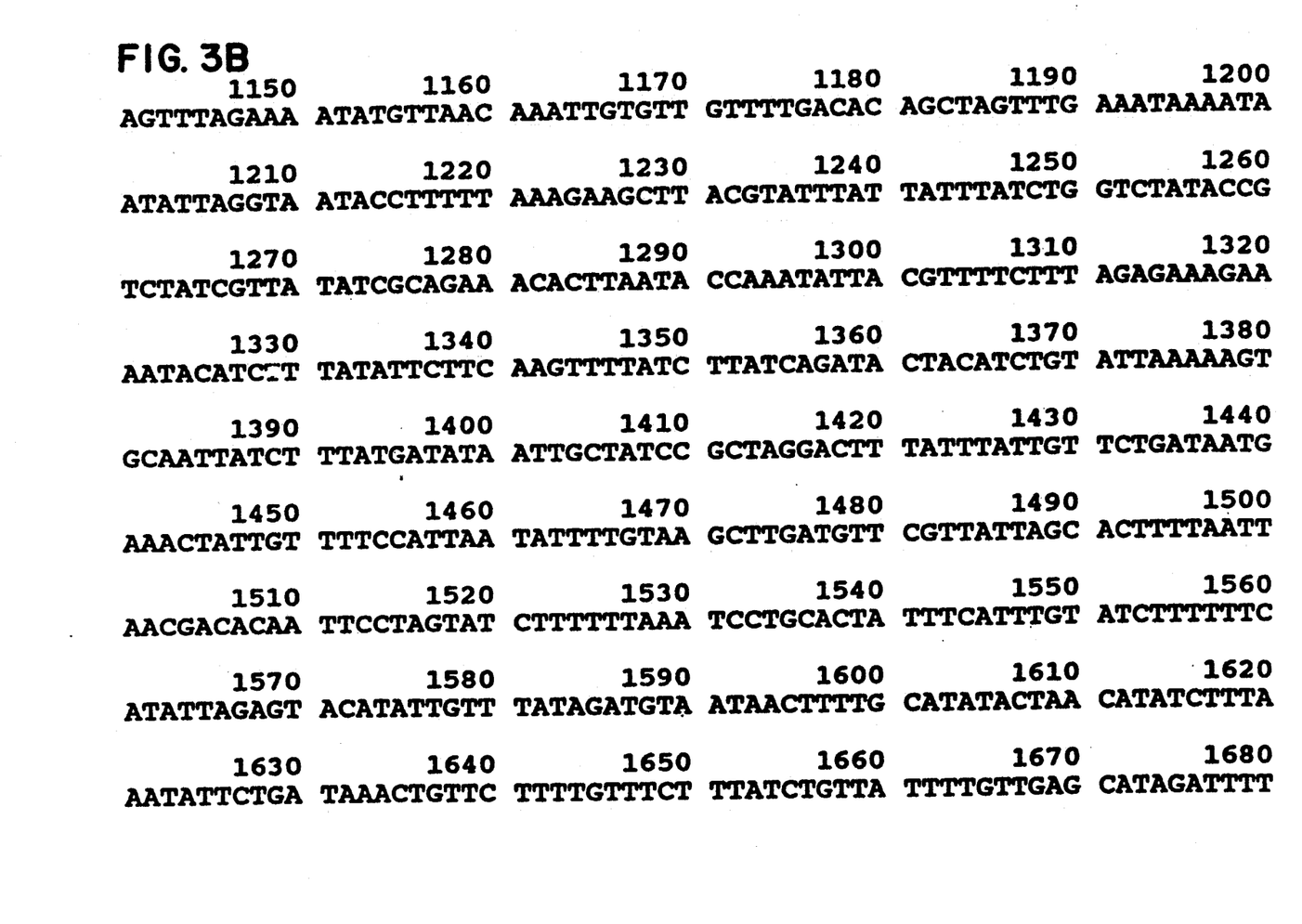
Figure 3C:
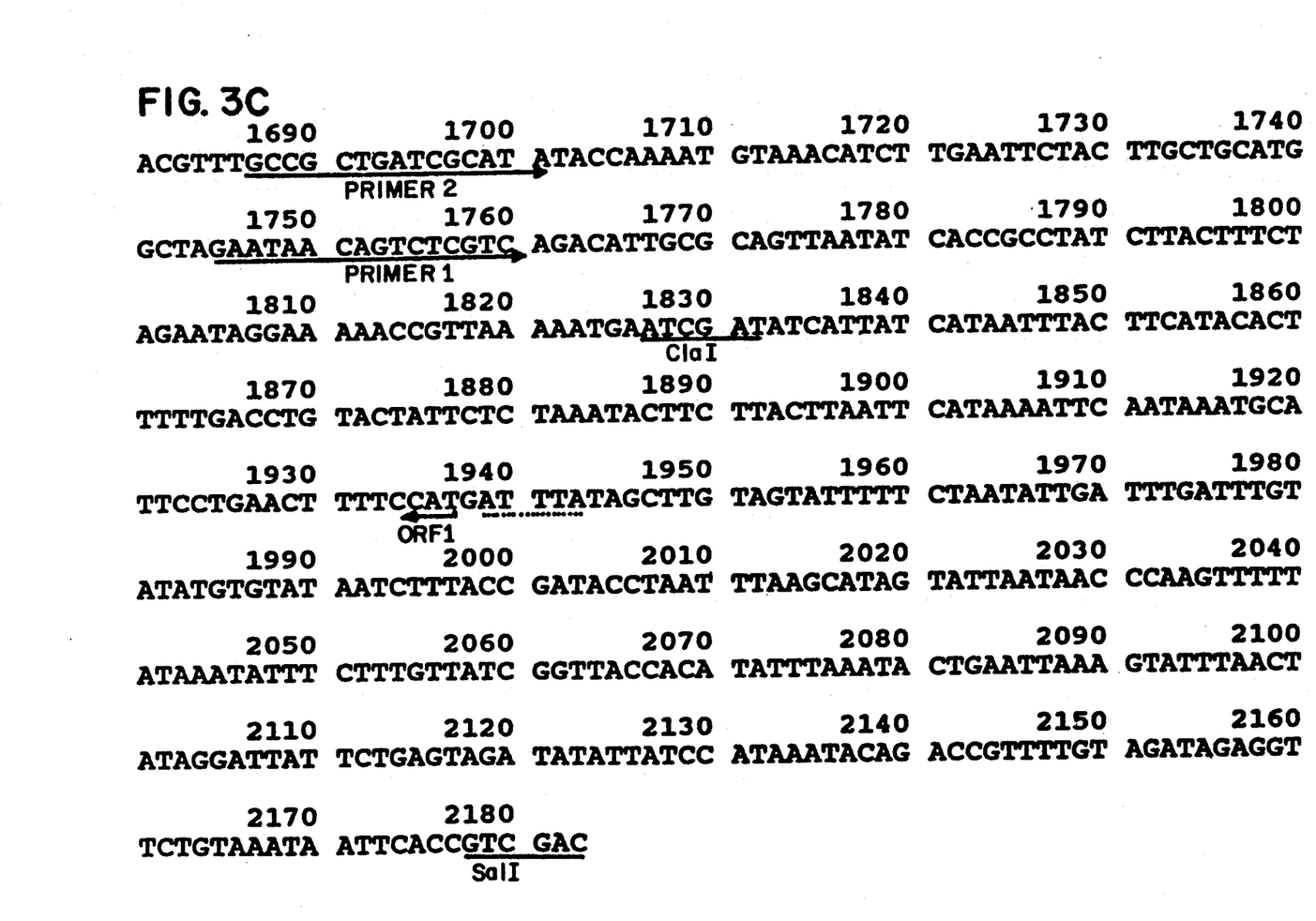
Figure 4:
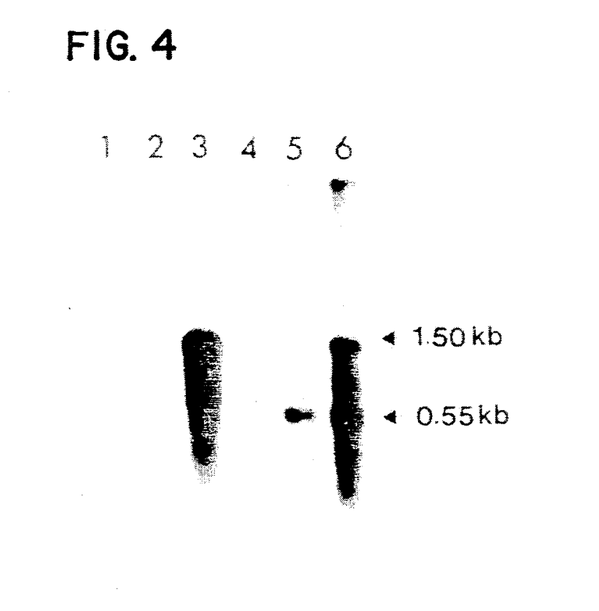

The 1.5 kb ClaI fragment was cloned into the AccI site of pUC 8, released as an EcoRI/Hind III fragment and recloned into M13 mp8 and mp9. The EcoRl and HindIII fragments of the clone were also subcloned into M13 vectors and the complete sequence of 1.5 kb ClaI fragment obtained by sequencing both strands is shown in FIG. 3. The sequence consisted of two open reading frames (ORF's), one (ORF1) extending beyond the ClaI site (1101 bp) and the other (ORF2) in the opposite orientation (501 bp) contained solely within 1.5 kb ClaI fragment. To ascertain which one of these ORF's codes for the early RNA, two single stranded M13 clones consisting of complementary strands of the 1.5 kb ClaI fragments were hybridized to early and late RNA from FPV infected cells, treated with S1 nuclease, electrophoresed on alkaline denaturing gels, transferred to nylon membranes and hybridised to nick-translated ClaI fragment. The mp8 clone (complementary to ORF1) protected a 1.5 kb late RNA while the mp9 clone (complementary to ORF2) protected one 0.55 kb early RNA and two 1.50 kb and 0.55 kb fragments with late RNA's. This indicated that ORF1 and ORF2 code for a late and an early/late transcript respectively. The 0.55 kb protected fragment late in the infection (FIG. 4, lane 6) possibly represents the presence of stable early message. The longer protected fragment of 1.5 kb in lane 6 could either be a transcript originating from the same start point as early transcript and terminating downstream of distal ClaI site, or a late transcript originating upstream of proximal ClaI site (upstream of the early gene initiation point). Since pox virus late genes lack defined termination signals, giving rise to transcripts with heterogenous 3' ends (Moss, 1985), the 1.5 kb protected fragment in lane 6 of FIG. 4 could have only originated from a late RNA start site near or upstream of the early start site. From S1 nuclease analysis (see below) it was apparent that the former possibility is true.

Analysis of the 5'-end of the ORF1 Coded RNA

Figure 5A:
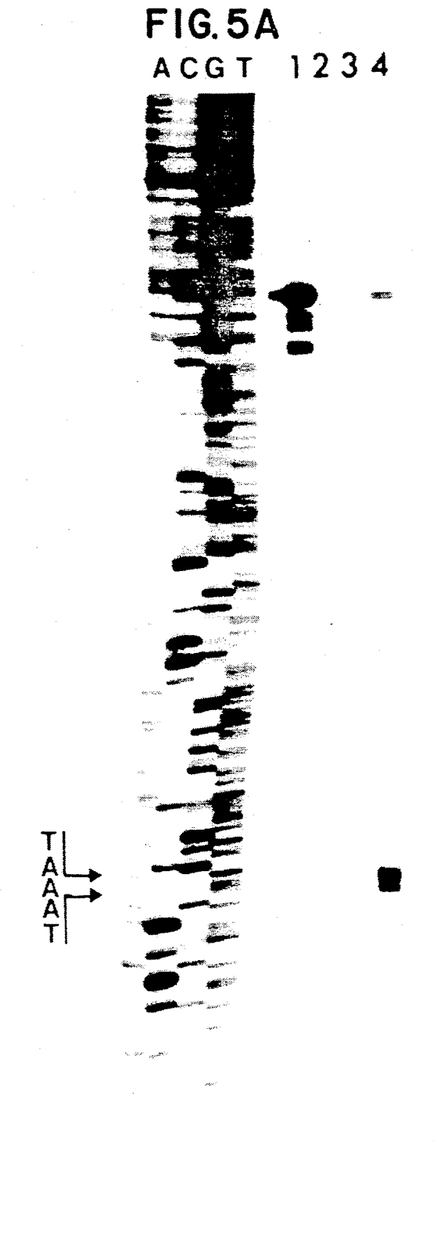
Figure 5B:
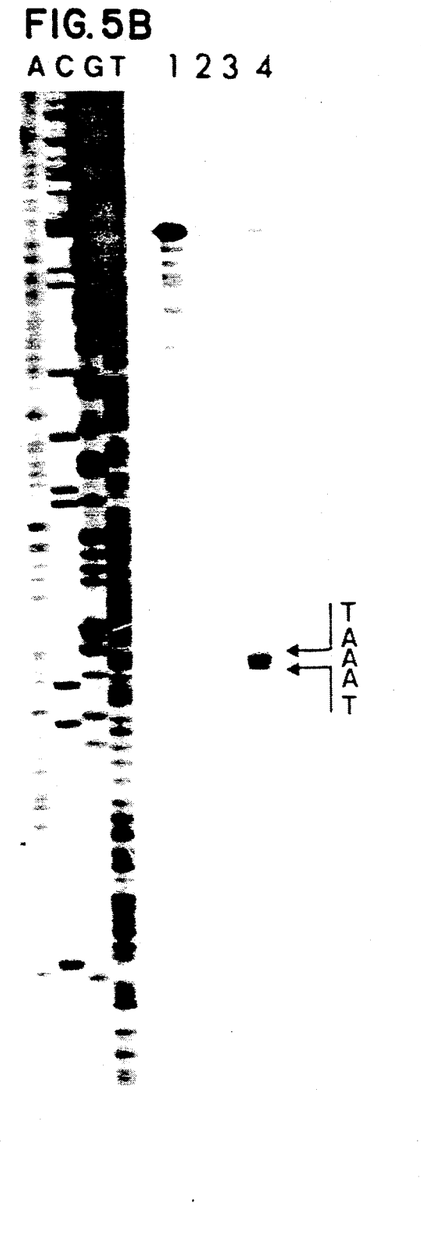

It was apparent from data presented earlier (FIG. 4) that ORF1 codes for a late RNA. In order to determine the 5'-end of this late gene, two synthetic oligomers complementary to late RNA like strand (Primers 1 and 2, FIG. 3) were extended on M13 clone consisting of the 3.7 kb SalI fragment (FIG. 1) in the presence of $^{32}$P-dCTP. ssDNA probes complementary to late transcript were hybridised to early and late RNA from FPV infected cells followed by S1 nuclease treatment (FIG. 5). It is clear from FIG. 5 that only late RNA protected the probe and the major protected product mapped to a 'TAAAT' sequence near the translation start site (FIG. 3).

Analysis of the 5'-end of the ORF2 Coded RNA's

Figure 6:
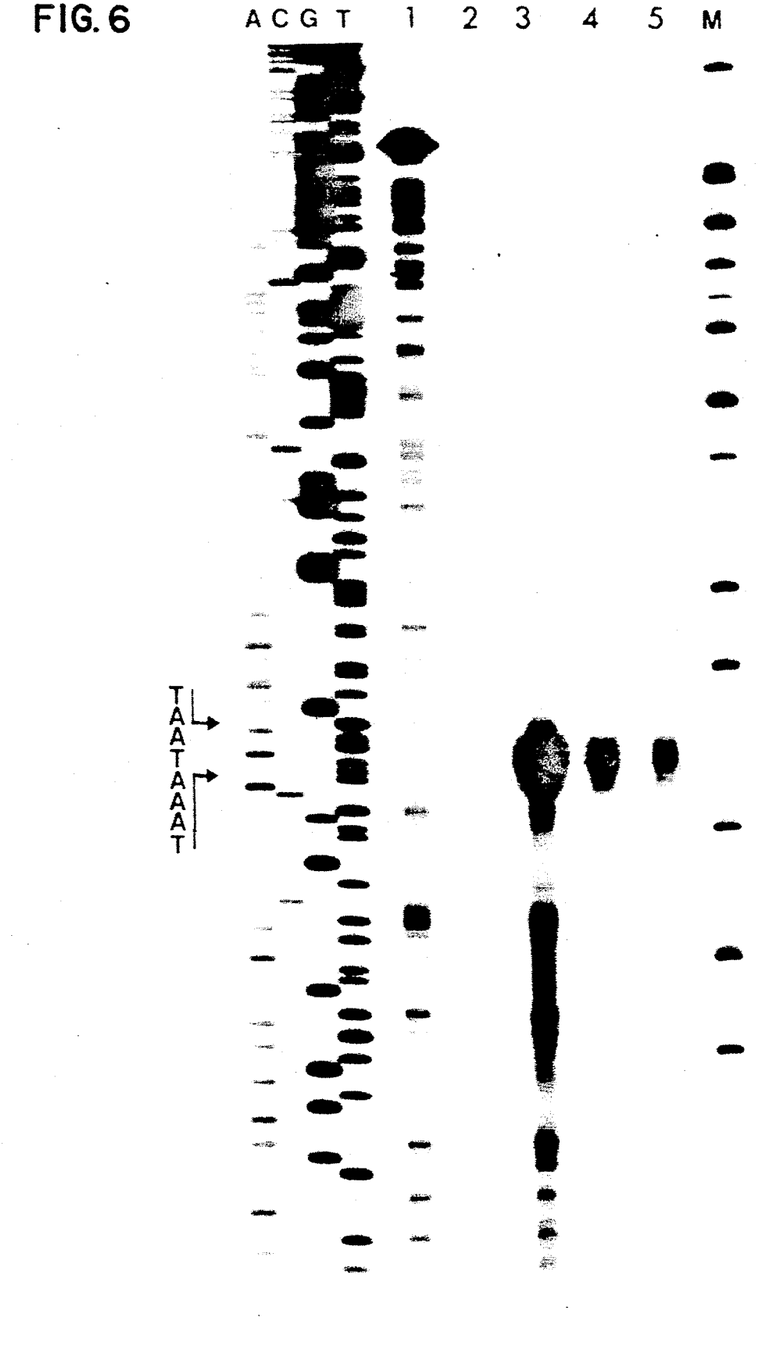

For the 5'-end analysis of the gene, a probe was prepared using a primer (primer 3, FIG. 3) upstream of the ClaI site and extending it on a ss-M13-Sal3.7 DNA clone which excompasses the complete ClaI fragment (FIG. 1). The 5'-end of the protected fragment by immediately early, early and late RNA mapped to a sequence TAAAT near the ATG of ORF2 (FIG. 6). Since there were no late RNA protected fragments of larger size, it appears that both early and late RNA shown in FIG. 4, initiate at the same start point. This is, to our knowledge, the first poxvirus promoter described where the same initiation site is recognised by RNA polymerase both during early and late stages of infection. However, the immediately early function of the gene appears to be the major aspect of the gene and for this reason and to avoid confusion, this promoter with early/late function has been referred as early promoter in the following text.

Presence of a Late Promoter Function Upstream and in Opposite Orientation to ORF2

Figure 7:
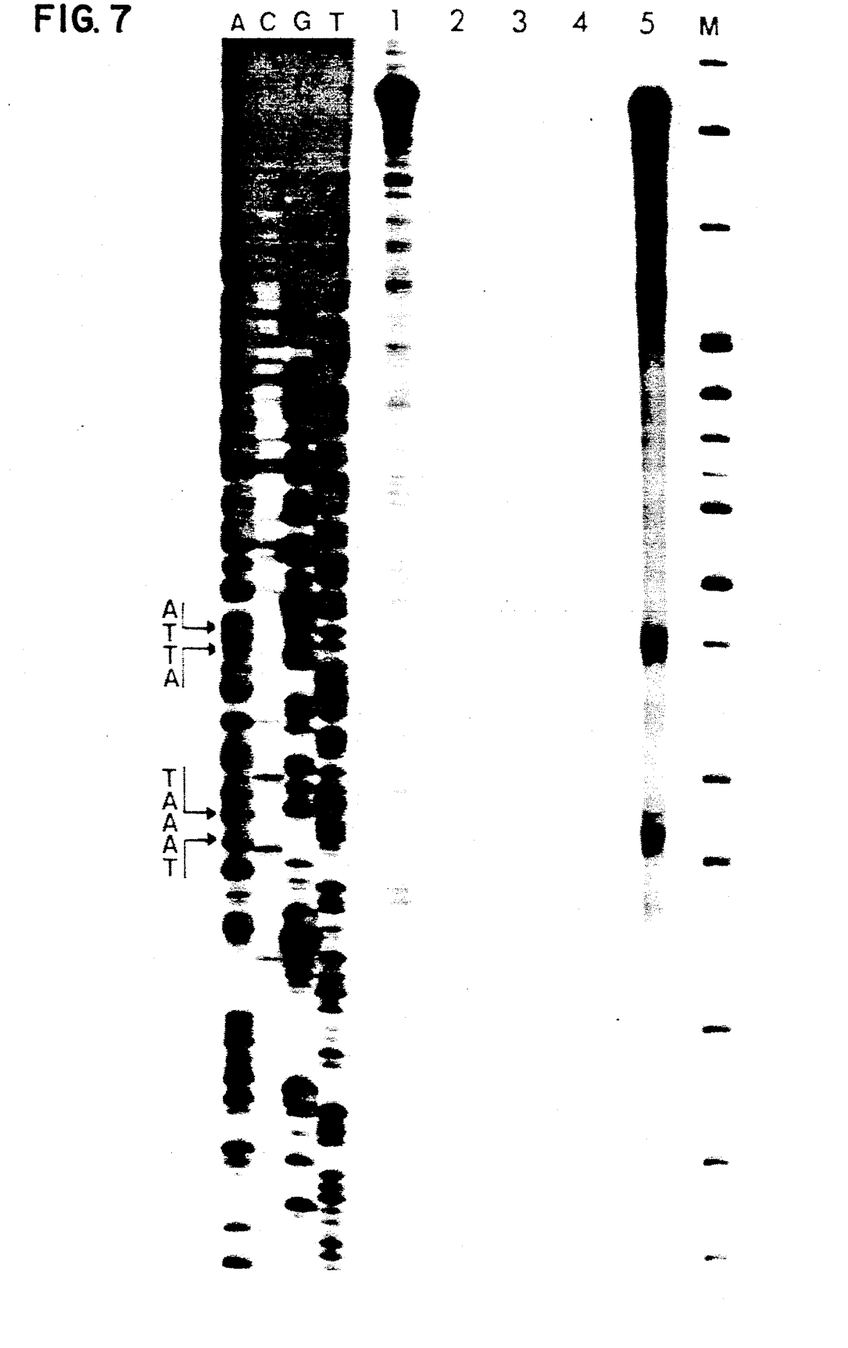

The sequencing of DNA upstream of the ClaI site revealed the presence of an ORF starting 35 bp from the early start site and in opposite orientation (ORF3, FIG. 3). The start of ORF3 consists of a 'TAAAT' motif, suggesting that it would transcribe a late mRNA. The S1 nuclease analysis of the 5'-end of this late gene revealed that only late RNA protected the probe from S1 digestion (FIG. 7). Major products mapped to the predicted 'TAAAT' motif upstream of the ATG while another major product mapped to a sequence 30 bp upstream (ATTA). There were several larger protected fragments all the way up to the size of probe and these possibly represent the heterogeneous 3'-ends of late transcript originating from ORF1. Since the late transcript maps to the sequence 30-35 bp upstream of the early start site, the sequence between the two start sites constituted a potential bidirectional promoter element, having both early/late and late function in opposite orientations.

40 bp of DNA are Sufficient for Expression of Both Early and Late Genes

Figure 8A:
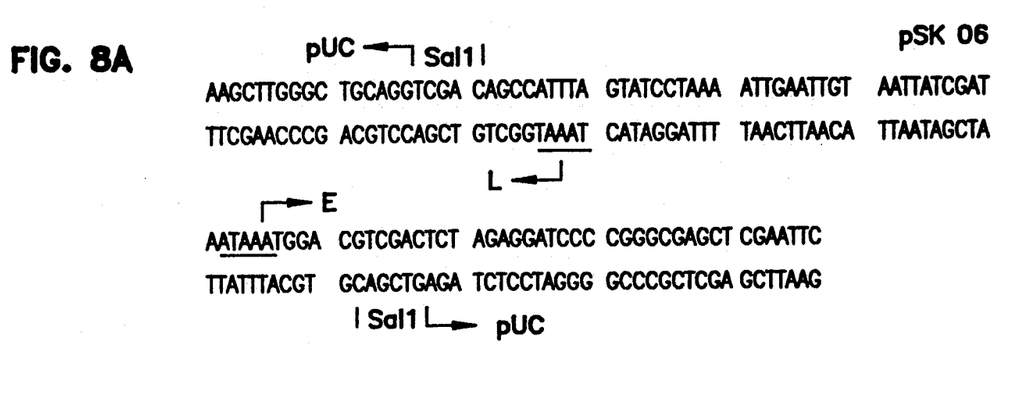

In order to assess the promoter activities, DNA sequence comprising of both early and late start sites and the first two amino acid codons (ATG and the following 3 bases) flanked by SalI linkers were synthesized and cloned into the SalI site of pUC12 in both orientations (FIG. 8). The first two codons of ORF's were included since the start site of both head to head genes map very close to the translation start site. A BamHI fragment from pGH101 consisting of a LacZ gene of *E. coli* (Herman et al., 1986) was then placed downstream of the promoter element (into the BamHI site) of pUC 12 linker. These vectors were designed in such a way that the ATG of LacZ was in frame with the ATG of the respective promoters (FIG. 8). These plasmids were then used in a VV transient expression system to assess the promoter strengths by the levels of B gal expressed (Table 2). The results indicated that high levels of B gal were expressed by the both early and late promoter elements. The temporal regulation of the promoter was also maintained and thus the early promoter activity was not affected by inclusion of AraC, and inhibition of DNA synthesis, while the late promoter activity was completely abolished (Table 2). Results also show that in CV-1 cells, the activity of early promoter is approximately 5-6 fold higher than that of late promoter. In a mutant of the early promoter where the region between ClaI and PstI site of pSK08 was deleted the activity of the early promoter was almost completely abolished (Table 2). Also deletion of 2 bp near the start site of late promoter abolished the activity of the late promoter (Table 2).

Assessment of the Activity of FPV—Early Promoter Relative to Vaccinia Virus Promoters Two widely used and well characterised promoters of VV, PL11 (late) and P7.5 (early/late) were used in a transient expression system to compare their activity with the FPV-early promoter. Constructs consisting of LacZ under control of PL11 (pDB22-LacZ) and P7.5 (pTP4) have been described and contain the LacZ-promoter chimera, flanked by either the FPV (pDB22-LacZ) or VV (pTP4) TK gene. pDB22-LacZ also contains an *E. coli* gpt gene under control of P7.5. Analogous plasmid constructs were made using the early promoter and LacZ gene, and used in the transient B-gal expression system. The results are shown in Table 3. It is clear from the data that the transfection of all plasmids result in significant amounts of B-gal activity in the transient expression system.

In pSK18, 20 and 22 where LacZ was placed under control of early-promoter element of FPV, flanked by either VV of FPV TK gene produce comparable B-gal activities. In the presence of AraC, an apparent accumulation of B-gal occurs, as was evident also from data in Table 2. Again the activity of late promoter element of FPV was about 1/5th of the early-promoter activity. When compared with two of the most used promoters of VV, P7.5 and PL11, the early-promoter activity was about 3.5 fold higher than that of P7.5 and approximately same to PL11. Since PL11 is the strongest known promoter of VV, the early FPV promoter is thus equally efficient. It is also clear from the data in Table 2 that the temporal regulation of all the promoters is maintained under transient expression conditions since in all cases, inhibition of DNA synthesis of AraC caused the block in late promoter activity. However, P7.5 an early/late promoter of VV only appeared to work late in the infection in our transient expression system, as has been observed by others (Chakrabarti et al., 1985).

Structure of the FPV Promoter Element

Figure 9:
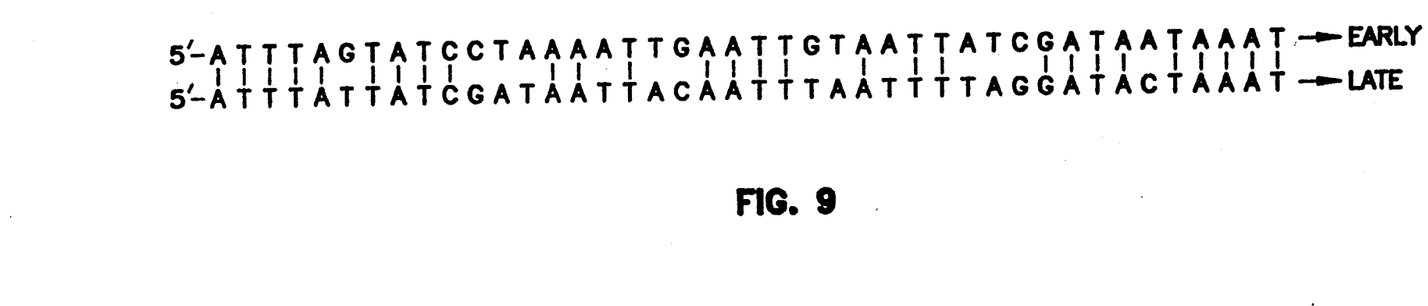
FIG. 9 is an alighment of early and late promoter elements of FPV.

It is clear from the data presented earlier that only 34 bp of DNA sequence between the early and late gene start sites (between 2-ATG's) is sufficient for the transcription of the early and late genes respectively. Since early and late promoters of pox viruses appear to be quite different (Smith et al, 1984) the FPV promoter element could be used in determining the DNA domains required for temporal regulation of pox virus early and late genes. It is evident from the results presented that a mutation near the early start site or within the TAAAT motif of late start site almost completely abolish their respective transcription function (Table 2). Pox virus late promoters are characterised by a highly conserved 'TAAAT' motif which is an essential cis acting element (Hanggi et al, 1986; Rosel et al, 1986). Thus the late promoter of FPV is similar to other reported pox virus late promoter elements. The interesting aspect of the FPV promoter element however is that early start site also maps to a TAAAT mofif. The 5'-3' alignment of the two strands of FPV promoter element show remarkable degree of similarity (FIG. 9). Out of 42 bases aligned, 28 bases match up perfectly without any deletion or substitution. The A-T content of the promoter element is 83% which is comparable to the sequences of other pox-virus promoters (Weir and Moss, 1983; Mars and Beaud, 1987; Lee-Chan et al, 1988). Besides this similarity, there are no remarkable DNA elements within the promoter region, upstream of RNA start site.

LITERATURE CITED

1. Moss, B. and Flexner, C., (1987) Annu. Rev. Immhnol. 5, 305–324.
2. Coupar, B. E. H. et al. (1986) Eur. J. Immunol. 16, 1479–1487.
3. Moss, B. (1985) In: Virology (Fields, B. N. ed.) pp. 685–703. Raven Press. New York and London.
4. Davis, L. G. et al. (1986) Basic method in molecular biology, Elsevier Science Publishing, New York.
5. Herman, G. E. et al. (1986) Nucleic Acids Res. 14, 7130
6. Chakrabarti, S. et al. (1985) Mol. Cell. Biol. 5, 3403–3409
7. Miller, J. H. (1872) Experiments in molecular genetics. Cold Spring Harbour Laboratory, Cold Spring Harbour, N.Y.
8. Smith, G. L. et al., (1984) Biotech. Genet. Engg. Rev. 2, 383–407
9. Hanggi, M. et al., (1986) EMBO J. 5, 7071–1076
10. Rosel, J. L. et al., (1986) J. Virol. 60, 436–449.
11. Weir, J. P. and Moss, B. (1983) J. Virol. 46, 530–537
12. Mars, M. and Beaud, G. (1987) J. Mol. Biol. 198, 619–631
13. Lee-Chen, G. J. et al., (1988) Virology 163, 64–79

TABLE 1

Approx. sizes of early transcripts hybridizing to four PstI fragments of FPV genome. Total cellular RNA isolated from FPV infected cells in presence of AraC was hybridized on northern blots to nick translated cloned PstI fragments of the FPV genome.

| PROBE | PstI fragment and its size (kb) | Approx. sizes of early transcripts (kb) |
|---|---|---|
| pTT55 | E (20.5) | 2.0, 1.7, 1.2 and 0.8 |
| pTT63 | F (17.3) | 3.2, 2.3, 1.3 and 1.0 |
| pTT28 | J (12.5) | 3.5, 2.4 and 1.7 |
| pTT68 | M (5.7) | Not detected |

TABLE 2

Figure 8B:
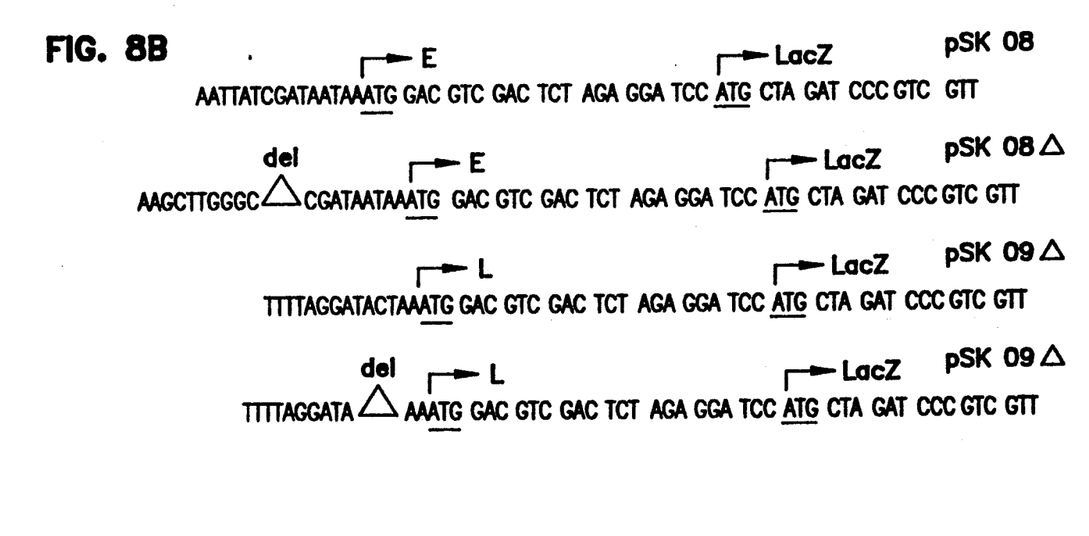
Figure 8C:
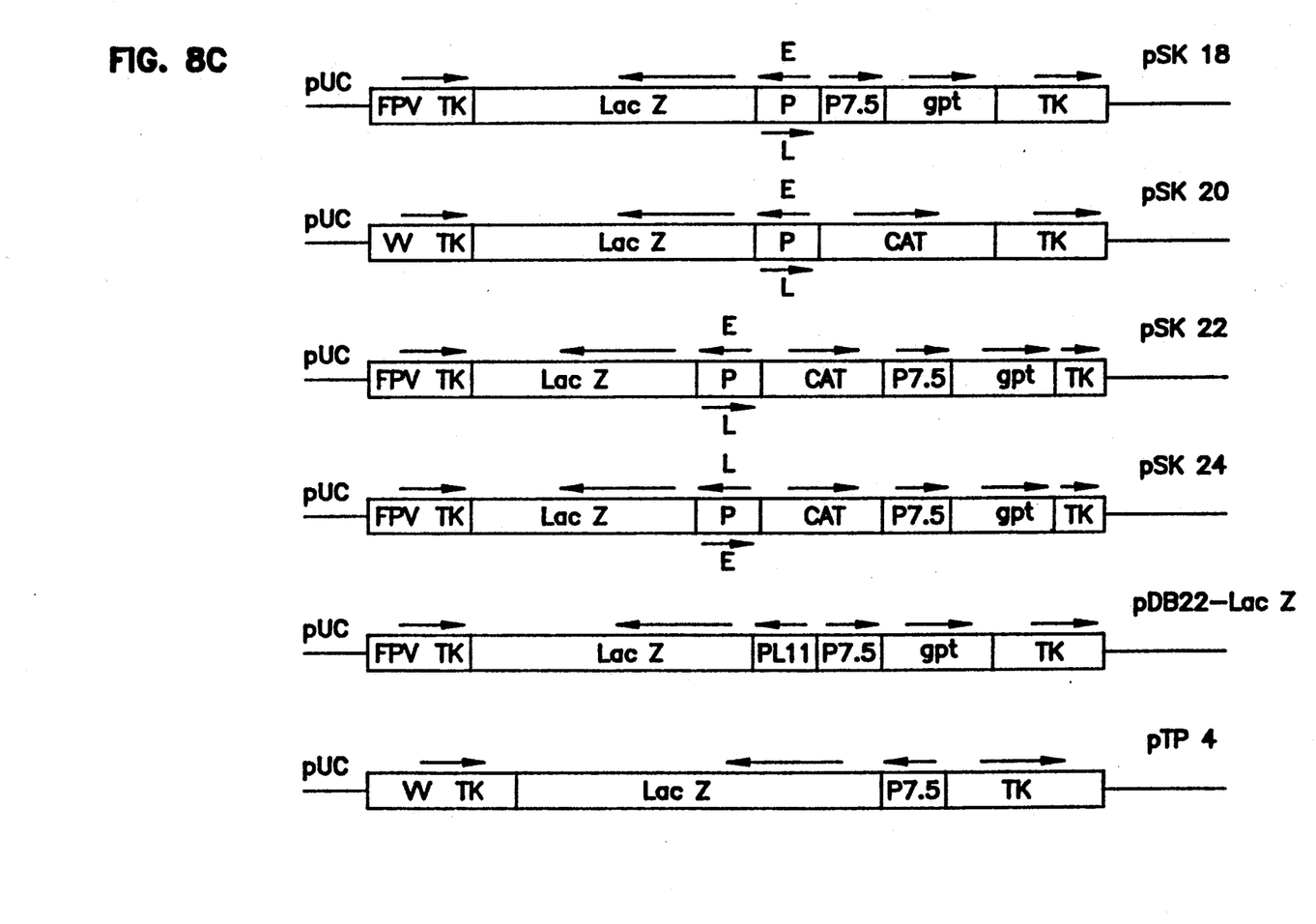

Activity of B-galactosidase in plasmid constructs in VV-transient expression system. E and L are Early and late promoter elements respectively and Δ represent mutations (see below). Transient expression experiments were carried out according to Chakrabarti et al (1985) using CV-1 cells and 25 ug of plasmid DNA. B-gal activity assayed by the method of Miller (1972) is expressed as umol of ONP produced/3 × $10^6$ cells/30 min at 28° C. The values represent mean of three estimations from the same experiment. pSK08 was generated by deleting the ClaI/PstI fragment of PSK08. In pSK09 two bases, (CT) near the RNA start site (TACTAAATG) have been deleted creating TAAAATG sequence (FIG. 8).

| Plasmid Construct | | B-gal activity | |
|---|---|---|---|
| | | −AraC (Late) | +AraC (Early) |
| pSK 08 | (LacZ - E) | 35.78 | 50.75 |
| pSK 08 | (LacZ - EΔ) | 0.13 | 0.00 |
| pSK 09 | (LacZ - L) | 6.50 | 0.27 |
| pSK 09 | (LacZ - LΔ) | 0.27 | 0.00 |

| | | |
|---|---|---|
| pSK 08 | (no virus infection) | 0.00 | 0.01 |

TABLE 3

Activity of B-galactosidase in plasmid constructs containing VV or FPV promoters in VV transient expression system. E and L are early and late elements of FPV promoter. Plasmids pSK20, 22 and 24 also contain a CAT gene opposite to LacZ. For details see text and FIG. 8. Experimental details are as in Table 2. B-gal activity is expressed as umol of ONP produced/3 × 10$^6$ cells/30 min at 28° C.

| Plasmid Construct | | B-gal activity | |
|---|---|---|---|
| | | −AraC (Late) | +AraC (Early) |
| pSK 18 | (LacZ - E, FPV-TK) | 25.10 | 34.44 |
| pSK 20 | (LacZ - E, VV-TK) | 26.70 | 32.50 |
| pSK 22 | (LacZ - E, FPV-TK) | 24.50 | 29.40 |
| pSK 24 | (LacZ - L, FPV-TK) | 4.6 | 0.27 |
| pTP4 | (LacZ - P7.5, VV-TK) | 7.2 | 0.4 |
| pDB22-LacZ | (LacZ-PL11, FPV-TK) | 24.8 | 0.27 |
| pSK 22 | (no virus) | 0.03 | 0.01 |

Finally, it is to be understood that various other modifications and/or alterations may be made without departing from the spirit of the present invention as outlined herein.

We claim:

1. An isolated bidirectional promoter element including a first promoter which controls expression of an early viral protein in fowlpox virus and a second promoter which controls expression of a late viral protein in fowlpox virus, said second promoter being in an opposite orientation to said first promoter, wherein said bidirectional promoter element has the sequence 5' AGCCATTTAGTATCCTAAAATTGAA
3' TCGG<u>TAAAT</u>CATAGGATTTTAACTT TTGTAATTATCGATAA<u>TAAAT</u>GGAC 3'
AACATTAATAGCTATTATTTACCTG 5'

2. A plasmid including
a plasmid cloning vector; and
a bidirectional promoter element including a first promoter which controls expression of an early viral protein in fowlpox virus and a second promoter which controls expression of a late viral protein in fowlpox virus, said second promoter being in an opposite orientation to said first promoter, wherein said bidirectional promoter element has the sequence 5' AGCCATTTAGTATCCTAAAATTGAA
3' TCGG<u>TAAAT</u>CATAGGATTTTAACTT TTGTAATTATCGATAA<u>TAAAT</u>GGAC 3'
AACATTAATAGCTATTATTTACCTG 5'

3. A plasmid according to claim 2, wherein the plasmid cloning vector is selected from plasmids pUC8, pUC12, M13-mp8 and M13-mp9.

4. A plasmid according to claim 2 selected from plasmids pSK06 and pCK07.

5. A viral vector including
a portion of the genome of a vector virus;
a bidirectional promoter element including a first promoter which controls expression of an early viral protein in fowlpox virus and a second promoter which controls expression of a late viral protein in fowlpox virus, said second promoter being in an opposite orientation to said first promoter, wherein said bidirectional promoter element has the sequence 5' AGCCATTTAGTATCCTAAAATTGAA
3' TCGG<u>TAAAT</u>CATAGGATTTTAACTT TTGTAATTATCGATAA<u>TAAAT</u>GGAC 3'
AACATTAATAGCTATTATTTACCTG 5' a first DNA sequence coding for a first foreign gene of interest and under the control of said first promoter; or
a second DNA sequence coding for a second foreign gene of interest and under the control of said second promoter; or
a first DNA sequence coding for a first foreign gene of interest and under the control of said first promoter together with a second DNA sequence coding for a second foreign gene of interest and under the control of said second promoter.

6. A viral vector according to claim 5, wherein the first foreign DNA sequence codes for a first antigen characteristic of an avian disease.

7. A viral vector according to claim 5, wherein the second foreign DNA sequence codes for a second antigen characteristic of an avian disease.

8. A viral vector according to claim 5, wherein the portion of the genome of a virus is a portion of the fowlpox virus genome or vaccinia virus genome.

9. A process for the preparation of a plasmid cloning vector which process includes:
(a) constructing a genomic library from DNA obtained from fowlpox virus DNA;
(b) isolating a bidirectional promoter element from the genomic DNA library, said bidirectional promoter element including a first promoter which controls the expression of an early viral protein in fowlpox virus and a second promoter which controls the expression of a late viral protein in fowlpox virus, said second promoter being in an opposite orientation to said first promoter, wherein said bidirectional promoter element has the sequence 5' AGCCATTTAGTATCCTAAAATTGAATTGTAATTATCGATAA<u>TAAAT</u>GGAC 3'
3' TCGG<u>TAAAT</u>CATAGGATTTTAACTTAACATTAATAGCTATTATTTACCTG 5'; and
and
(c) inserting the bidirectional promoter element into a suitable site in a plasmid cloning vector.

* * * * *